United States Patent [19]

Andersson et al.

[11] E Patent Number: Re. 32,718

[45] Reissued Date of Patent: Jul. 26, 1988

[54] TRANSILLUMINATION DIAGNOSTIC METHOD AND APPARATUS

[75] Inventors: Torsten Andersson, Eslov; Bjorn Ohlsson, Veberod, both of Sweden

[73] Assignee: Sinus Medical Equipment AB, Skelleftea, Sweden

[21] Appl. No.: 573,614

[22] Filed: Jan. 25, 1984

Related U.S. Patent Documents

Reissue of:

[64] Patent No.: 4,312,357
Issued: Jan. 26, 1982
Appl. No.: 104,392
Filed: Dec. 17, 1979

U.S. Applications:

[63] Continuation-in-part of Ser. No. 857,696, Dec. 5, 1977, abandoned.

[30] Foreign Application Priority Data

Dec. 3, 1976 [SE] Sweden ..... 7613587

[51] Int. Cl.[4] ..... A61B 6/12

[52] U.S. Cl. ..... 128/664; 128/23; 128/633; 250/330; 356/51

[58] Field of Search ..... 128/633, 664, 665, 23, 128/395–398; 354/62, 126; 250/341, 330, 492.1, 493.1; 356/51

[56] References Cited

U.S. PATENT DOCUMENTS

| | | | |
|---|---|---|---|
| 2,866,900 | 12/1958 | Busignies et al. | 250/341 |
| 2,902,911 | 9/1959 | Novori | 351/7 |
| 3,152,587 | 10/1964 | Ullrich et al. | 128/633 |
| 3,245,402 | 4/1966 | Barnes | 128/664 |
| 3,318,216 | 5/1967 | Hajjar et al. | 354/62 |
| 3,463,142 | 8/1969 | Hark | 128/633 |
| 3,527,932 | 9/1970 | Thomas | 128/32 |
| 3,597,616 | 8/1971 | Brunton | 250/341 |
| 3,638,640 | 2/1972 | Shaw | 128/633 |
| 3,648,685 | 3/1972 | Hepp et al. | 128/665 |
| 3,664,730 | 5/1972 | Cardona | 351/16 X |
| 3,674,008 | 7/1972 | Johnson | 128/665 |
| 3,704,706 | 12/1972 | Herczfeld et al. | 128/633 |
| 3,777,738 | 12/1973 | Sugita et al. | 128/664 |
| 3,867,041 | 2/1975 | Brown et al. | 250/341 |
| 3,930,158 | 12/1975 | Chicklis et al. | 250/330 |
| 3,954,329 | 5/1976 | Pomerantzeff | 351/16 |
| 4,077,399 | 3/1978 | Le Roy | 128/23 |

FOREIGN PATENT DOCUMENTS

| | | | |
|---|---|---|---|
| 2236130 | 1/1974 | Fed. Rep. of Germany | 128/664 |
| 2449060 | 4/1976 | Fed. Rep. of Germany | 128/664 |
| 2538985 | 5/1976 | Fed. Rep. of Germany | 128/633 |
| 197852 | 11/1967 | U.S.S.R. | 128/664 |

*Primary Examiner*—Edward M. Coven
*Assistant Examiner*—Max F. Hindenburg
*Attorney, Agent, or Firm*—Burns, Doane, Swecker & Mathis

[57] ABSTRACT

An instrument for indicating anomalies in human tissue comprises first and second light emitters. The first light emitter comprises a tungsten filament which transilluminates the tissue and visually indicates any anomalies therein. The second light emitter emits a light of higher intensity than the light from the first emitter. The second emitter is actuated while the tissue is being transilluminated by the first light emitter to make an exposure on infrared sensitive film located at an opposite side of the tissue.

7 Claims, 2 Drawing Sheets

TRANSILLUMINATION DIAGNOSTIC METHOD AND APPARATUS

Figure 1:
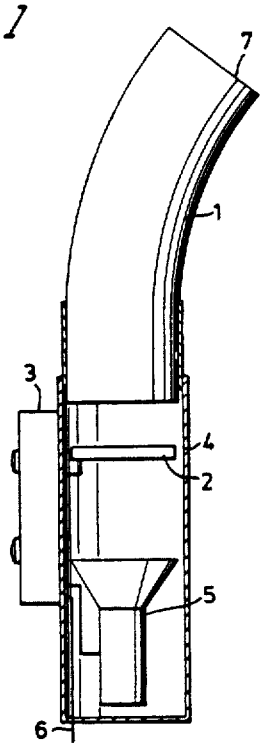

Matter enclosed in heavy brackets [ ] appears in the original patent but forms no part of this reissue specification; matter printed in italics indicates the additions made by reissue.

This is a Continuation-In-Part of U.S. Ser. No. 857,696, filed on Dec. 5, 1977 by Torsten Andersson and Bjorn Ohlsson, and now abandoned.

The present invention relates to a method of in situ diagnosticating pathological changes in human tissue, and in particular in breast tissue, and a device for carrying out the method.

It is well known in the art that distinct indications of cancer in, for example, human breast tissue, can only be positively obtained prior to surgical removal of the tissue by cytological examination of a small extracted sample. The extraction is effected by means of a needle, which must be inserted into the tissue accurately in order to reach the location of the suspected tissue.

Hitherto it has only been possible to extract samples accurately for cytological examination, by directing the needle for removal of the sample during continuous X-ray examination. This is a very difficult procedure and in a very large percentage of cases the cytological tests are negative and it has only been possible to practice the method where a rather high expectancy of cancer exists. The extraction of samples during continuous X-ray examination is not a readily acceptable method, since it may involve a cancer risk per se.

Because of this it has been proposed to transilluminate the tissue, such as the breast of a woman, with a light source, and optionally to photograph the transilluminated tissue. Since the wave lengths of the light transmitted and the wave lengths of the light absorbed were not previously exactly known, it has not been possible to make visual observations and photographic recordings successfully. It has also been proposed to transilluminate the tissue in semi-darkness, with the aid of a very powerful light-source against a blue background illumination. The disadvantage with this method is that the eye is forced to observe spectra of widely differing wave-lengths, namely the blue background illumination and the red image of the tissue. These two light effects greatly impair the possibility of the eye to discern contrasts, and consequently the illuminated tissue cannot be observed visually with any degree of certainty. The greatest problem, however, is that a pathological change in the tissue, e.g. a cancer growth, can only be perceived with great difficulty. When the tissue is transilluminated with blue light, the light will be greatly absorbed by the blood in the tissue, as later illustrated, and an anomaly in the form of, for example, a cancerous growth which contains a collection of blood will appear as a spot during said transillumination. The appearance of the spot to the human eye is based on the information found within the wave-length of 600–700 nm, since practically all light beneath 600 nm is absorbed by the blood in the breast tissue and the sensitivity of the eye is practically zero at about 700 nm. The degree of uncertainty is then such as to necessitate an X-ray examination. Attempts to photograph the transilluminated tissue with a black and white sensitive film or a colour film in order to facilitate investigation of the image have failed, since conventional colour film, for example, has no appreciable sensitivity over wave-lengths between 600–700 nanometers.

Consequently the prime object of the invention is to provide a novel method of in situ diagnosticating pathological changes in body tissue. The novel method is mainly based on the steps of transilluminating the body tissue by means of a low-intensity light source arranged to generate light within the whole of the visible spectrum and preferably within the range of 400–1000 nm. The lamp has a tungsten filament and, for example, is of the type sold by Philips under the designation 12105N and having a power of about 20 watts. The light from this lamp is transmitted into the body tissue by means of a shielded light conductor, for example a homogenous acrylic rod or a flexible fibre optic rod. One end of this light conductor is irradiated by the light source and the other end is held against one side of the body tissue. The non-filter light is spread uniformly through the body tissue and the resultant image can be observed from the other side of the tissue. The transmission of light is substantially constant within the whole of the spectral range of the tissue in question, while the veins, arteries, changes in tissue etc. which contain blood will absorb light within the blue-green part of the spectrum, the absorption being less within the range of 600–1000 nm. The absorption of light by the blood within the range of 550–580 nm becomes particularly noticeable. Thus, tissue containing much blood will be a very dark red, or almost black colour, thereby rendering it impossible to visually observe any details, since the eye is sensitive only in the range of 400–600 nm. Consequently, in order to produce a detailed image of the tissue and its changes it is necessary to select a wave-length range within the red spectrum, i.e. within a range exceeding 600 nm. Experiments have shown that the difference in transmission within a wavelength range of, for example, 600–900 nm in respect of body tissue as such, and blood, is sufficient to obtain a requisite contrast, i.e. it shall be possible to differentiate the form and nature of the tissue from that of blood. The eye, however, is not capable of detailed discernment and consequently there is used in accordance with the invention a colour film which is also sensitive to light within the infrared range, i.e. within a range of about 650–900 nm. The film is held in a manner such that the plane of the film lies substantially in a plane which intersects the axial extension of the light conductor perpendicularly, i.e. lies parallel with the surface of the light conductor lying against the tissue when said surface is planar. The film is then exposed with a flash lamp and the high intensity of the lamp, which transmits light through the whole of the visible spectrum, exposes the film very rapidly, for example in 1/60th of a second. Since the colour film used is also sensitive to infrared light, i.e. light within the range of 650–900 nm, as is the case with a colour film sold by Kodak under the name Kodak Electrochrome Infrared, and the difference in transmission between body tissue as such and blood is sufficient to enable all details which cannot be observed by the human eye to be clearly registered on the exposed infrared-sensitive film, there is obtained a clear and succinct documentation of the appearance of the tissue, thereby often rendering it unnecessary to take surgical steps for ascertaining the changes in the tissue.

The novel method according to the invention is carried out by means of a device comprising two light sources, of which one is used to visually observe shadowy anomalies in the image of the transilluminated tissue, and the other comprises a flash lamp for recording said image photographically on a colour film, the two light sources being arranged to illuminate, independently of one another, the input end of a light conductor for transmitting light to the body tissue to be examined. The output end of the light conductor is arranged to be brought into contact with the body tissue to be transilluminated, and can be aligned onto anomalies in the body tissue by means of the light source used for visual illumination, said light source being of low intensity and emitting unfiltered light through the blue to the infrared wave-length region of the spectrum. The photographic film is mounted in a camera and consists of a colour film which is sensitive to infrared light and which is arranged to be exposed by activating the flash lamp, which emits unfiltered light within the blue to the infrared region of the spectrum.

Figure 2:
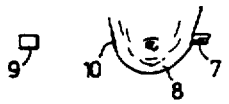
Figure 3:
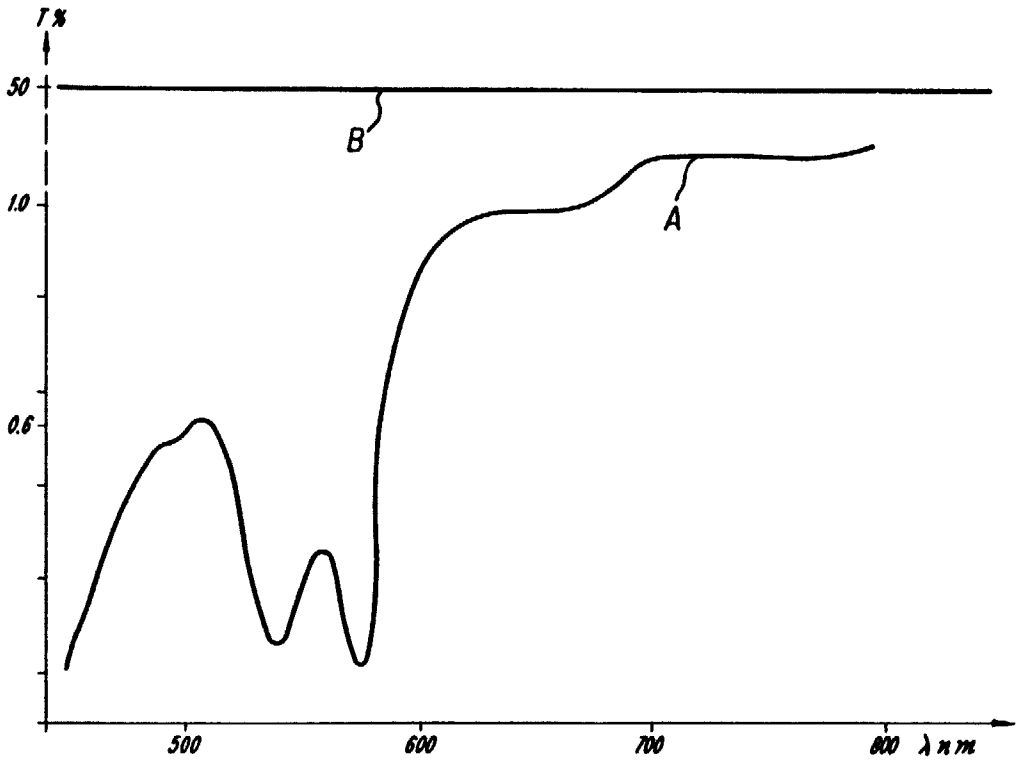

The method and the device will now be described with reference to the accompanying drawing, in which FIG. 1 is a sectional view of an illuminating device constructed in accordance with the invention, FIG. 2 shows very schematically the manner in which the illuminating device of FIG. 1 is used when taking photographic pictures, and FIG. 3 is a blood transmission curve plotted in respect of an exemplary sample of tissue.

The reference 1 identifies a light-conducting member which in the illustrated embodiment comprises a curved and optionally flexible rod of a transluminent plastics material, such as acrylic resin, said rod being of circular cross-section and having an end surface 7 arranged to be pressed against the region of body tissue to be examined, such as the breast 8 of a woman. The member 1 is covered with a thin layer of an opaque material, with the exception of its end surfaces. One end of the member 1 is inserted into a cylindrical housing 4 provided with a control box 3. The housing 4 is manufactured of an opaque material and includes two light sources 2,5, of which one is an incandescent lamp 5 arranged to be energized from a conventional, variable voltage source (not shown) arranged in the box 3. The other light source comprises an electronic flash source 2 arranged to be activated by means of devices (not shown) in the box 3 and which is synchronized with the shutter of a camera 9. The camera is located on the side of said region of tissue to be examined remote from the light source. The reference 6 identifies a flexible power-supply cable.

When differentially diagnosticating pathological changes in human tissue in accordance with the method of the invention, the aforedescribed device is used in the following manner:

The free end 7 of the light-conducting member 1 is held, for example, against the underside of a breast 8 to be examined. The incandescent lamp 5, which is of low intensity, is ignited and emits light within the whole of the visible spectrum and in all events within the blue to the infrared region of the spectrum. The light is diffused and spread in the body tissue, which is a requirement which must be fulfilled in order for an assessment to be made. The lamp is energized to such power as to obtain a transillumination of the breast. It is now possible to visually detect in the form of shadows anomalies in the breast tissue, which shadows are manifested by light which lies within the range of between 600 and 700 nm, since blood absorbs light of shorter wave-lengths, but it is not possible to detect whether the anomalies are due to breast cancer or not, because the details are not clearly discernable. The light-conducting member 8 is held in a position such as to obtain the clearest visual picture of the shadow, and the camera 9 is loaded with a film which is also sensitive to light within the red spectrum, whereafter the camera is aligned onto the shadowed area at a distance of approximately 30 cm from the surface 10 of the breast, on the opposite side thereof to the side to be illuminated. The film is now exposed by igniting the flash device 2. The flash device, which is highly intensive thereby to provide a short exposure of the infrared-sensitive film in the camera 9, emits light within the blue to the infrared area of the spectrum and, is completely unfiltered, similar to the light from the incandescent lamp 5, which lamp includes a tungsten filament. The lamp 5 may be ignited or extinguished when exposing the film [9'] in the camera 9. The film is exposed with the camera 9 in a position such that the plane of the film [9'] is substantially perpendicular to the output axis [11] of the light conductor 1.

The developed coloured film will show the previously shadowy or black portions in colour and the normal breast tissue in a yellow colour while the fibroadenomatosis or other blood-filled anomalies are shown clearly as light-red or dark-red spots. In certain cases such spots cannot be discovered with X-rays, even though the anomaly may have been palpably detected. Cysts containing clear, uncoloured liquid will appear as a light halo or rounded change against the background of the normal, yellow breast tissue. Dark spots on the coloured photograph indicate anomalies of a serious nature. Since the method may be performed within a short period of time, 3–4 minutes, without photographic registration and about 15 minutes if a coloured photograph is to be taken, and without any nuisance to the person being examined, it is very suitable for routine controls of unscreened populations. The incandescent lamp 5 used is preferably provided with a tungsten filament and is, for example, of the kind mentioned in the introduction.

In the case of detected anomalies, a needle extraction of tissue samples for cytological tests may be carried out while using the device according to the invention. The device enables the unhealthy change or anomaly to be localized extremely distinctly, and a sample of tissue can be extracted by comparing the actual visual picture with a previous photographic registration. The photographic registration will, of course, be of great importance during any subsequent surgical treatment of the patient.

FIG. 3 illustrates in simplified form a transmission curve A for blood and a transmission curve B for tissue as such. The vertical axis shows the light transmission in percent of light supplied and the horizontal axis shows the wave-length of the light. It should be noted that the curve B has been plotted in respect of a very thin tissue sample and is only intended to show that the transmission through body tissue of normal type is substantial constant irrespective of the wave-length of the light. If thick tissue is transilluminated, the curve B will be moved vertically downwards.

The invention provides for a positive analysis of suspected changes in body tissues, which can be traced by transillumination and visual observation but which can not be determined with any certainty but merely indicated that closer examination must be made. By using a colour film which is also sensitive to infrared light, and thereby enabling a region of the spectrum which cannot be observed with the naked eye to be used, there is obtained firstly a detailed image of the tissue as such and secondly a detailed image of the blood-filled portions of the tissue. The photograph obtained is the basis of an exact or at least relatively exact diagnosis of the unhealthy changes, thereby eliminating the necessity of X-ray radiation and the taking of tissue samples. It should be noted that all anomalies in body tissue can be detected by means of the novel method, such as liquid-filled cysts.

We claim:

1. A method of in situ differentially diagnosing pathological changes in human body tissue, comprising the steps of:

directing towards one side of the body tissue a shielded light transmitting instrument;

actuating a first low intensity light emitter in said instrument which comprises a tungsten filament, and which emits light from within the blue to within the infrared spectrum, which transilluminates the body tissue and visually indicates the presence of any anomalies in the tissue, arranging infrared sensitive film at the opposite side of the body tissue, and actuating a second light emitter emitting light from within the blue to within the infrared spectrum in said instrument to emit a second light of higher intensity than the light from said first emitter whereby light passing through the tissues makes an exposure on said infrared sensitive film.

2. A method according to claim 1, wherein said step of actuating a second light emitter comprises the step of actuating a flash lamp.

3. An instrument in combination with infrared sensitive film for detecting pathological changes in human body tissue, comprising:

a shielded light transmitting member having one end suitable for application against one side of human body tissue being examined, a low-intensity light source emitting light from within the blue to within the infrared spectrum and located at the other end of said transmitter member and comprising:

(*1*) a first light emitter comprising a tungsten filament for emitting a diffuse light which transilluminates the body tissue and visually indicates the presence of any anomalies in the tissue, and (*2*) a second light emitter for emitting a second light from within the blue to within the infrared spectrum of higher intensity than the light from said first emitter, for making an exposure on the infrared sensitive film located at the opposite side of the tissue.

4. An instrument according to claim 3 wherein said second light emitter comprises a flash lamp.

5. A method according to claim 1, wherein said film is spaced from said tissue when the exposure is made.

*6. A method of in situ differentially diagnosing malignant tissue in human body tissue, comprising the steps of arranging infrared sensitive image generating means on one side of the body tissue, and directing toward the opposite side of the body tissue a light which includes light within the infrared spectrum so that light passing through the tissue is sensed by said infrared sensitive image generating means to produce an image for delineating the existence and location of maglignant tissue in the body tissue.*

*7. The combination of infrared sensitive image generating and illuminating means for detecting malignant tissue in human body tissue, said illuminating means comprising a light transmitting member having one end suitable for direction toward a side of human body tissue disposed opposite a side thereof where said infrared sensitive image generating means is disposed, and a light source including a light emitter for emitting a light which includes light within the infrared spectrum for being sensed by said infrared sensitive image generating means after passing through the body tissue, in order to produce an image for delineating the existence and location of malignant tissue in the body tissue.*

* * * * *